(12) United States Patent
Zuber

(10) Patent No.: US 12,233,204 B2
(45) Date of Patent: Feb. 25, 2025

(54) NICOTINE POWDER DELIVERY SYSTEM

(71) Applicant: PHILIP MORRIS PRODUCTS S.A., Neuchâtel (CH)

(72) Inventor: Gérard Zuber, Boulens (CH)

(73) Assignee: Philip Morris Products S.A., Neuchâtel (CH)

( * ) Notice: Subject to any disclaimer, the term of this patent is extended or adjusted under 35 U.S.C. 154(b) by 63 days.

(21) Appl. No.: 17/732,661

(22) Filed: Apr. 29, 2022

(65) Prior Publication Data

US 2022/0249786 A1 Aug. 11, 2022

Related U.S. Application Data

(62) Division of application No. 16/064,173, filed as application No. PCT/IB2016/057455 on Dec. 8, 2016, now Pat. No. 11,338,099.

(30) Foreign Application Priority Data

Dec. 24, 2015 (EP) .................................... 15202712

(51) Int. Cl.
*A61M 15/00* (2006.01)
*A24F 42/20* (2020.01)
(Continued)

(52) U.S. Cl.
CPC .......... *A61M 15/0035* (2014.02); *A24F 42/20* (2020.01); *A24F 42/60* (2020.01); *A61M 15/0008* (2014.02); *A61M 15/0021* (2014.02); *A61M 15/003* (2014.02); *A61M 15/0063* (2014.02); *A61M 15/06* (2013.01); *A61M 2202/064* (2013.01); *A61M 2206/16* (2013.01)

(58) Field of Classification Search
CPC .......... A61M 15/0035; A61M 15/0008; A61M 15/003; A61M 15/0063; A61M 15/06; A61M 2202/064; A61M 2206/16; A61M 15/0021; A24F 42/20; A24F 42/60; A24F 40/40; A24F 40/20
See application file for complete search history.

(56) References Cited

U.S. PATENT DOCUMENTS 4,069,819 A * 1/1978 Valentini ........... A61M 15/0033
604/131
4,695,274 A 9/1987 Fox
(Continued)

FOREIGN PATENT DOCUMENTS

CN 2742785 11/2005
CN 101888867 11/2010
(Continued)

OTHER PUBLICATIONS

Japanese Office Action for JP Application No. 2021-128118, issued by the Japanese Patent Office on May 23, 2022; 11 pgs. including English translation.
(Continued)

*Primary Examiner* — Joseph D. Boecker
(74) *Attorney, Agent, or Firm* — Mueting Raasch Group

(57) ABSTRACT

A nicotine powder delivery system includes an inhaler article and a nicotine powder capsule disposed within the inhaler article. The nicotine powder capsule rotates about a longitudinal axis when air flows through the inhaler article.

20 Claims, 2 Drawing Sheets

Figure 1:
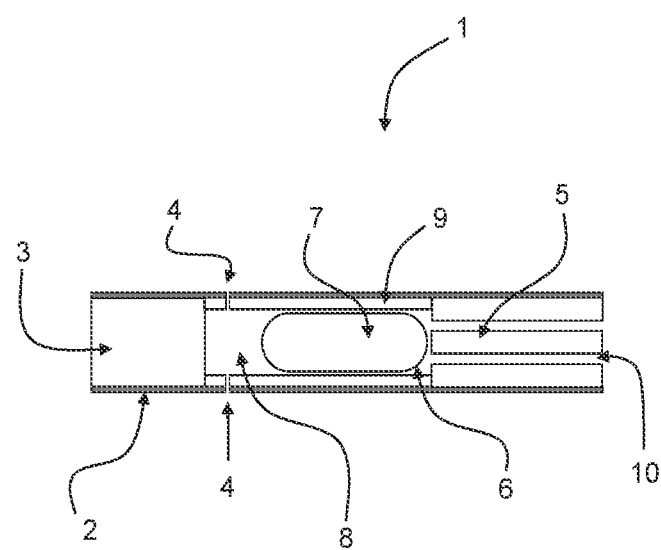

(51) Int. Cl.
*A24F 42/60* (2020.01)
*A61M 15/06* (2006.01)

(56) References Cited

U.S. PATENT DOCUMENTS

| | | | |
|---|---|---|---|
| 4,735,217 A | | 4/1988 | Gerth et al. |
| 4,790,305 A | * | 12/1988 | Zoltan ............... A61M 15/0088 128/200.23 |
| 4,995,385 A | | 2/1991 | Valentini et al. |
| 5,042,510 A | * | 8/1991 | Curtiss .................... A24F 42/20 131/272 |
| 5,746,227 A | | 5/1998 | Rose et al. |
| 6,102,036 A | * | 8/2000 | Slutsky ................. A61M 15/06 128/202.21 |
| 6,681,768 B2 | | 1/2004 | Haaije de Boer et al. |
| 8,561,609 B2 | | 10/2013 | Donovan et al. |
| 8,813,759 B1 | * | 8/2014 | Horian .................... A24F 42/60 131/273 |
| 10,207,066 B2 | | 2/2019 | Dunkley et al. |
| 10,668,058 B2 | | 6/2020 | Rose et al. |
| 10,912,334 B2 | * | 2/2021 | Zinovik ............ A61M 15/0028 |
| 10,932,492 B2 | * | 3/2021 | Zinovik ................. A61M 15/06 |
| 11,878,114 B2 | * | 1/2024 | Zinovik ................. A24F 42/20 |
| 2003/0015195 A1 | * | 1/2003 | Haaije de Boer ......................... A61M 15/0086 128/203.15 |
| 2004/0206350 A1 | | 10/2004 | Alston et al. |
| 2005/0000518 A1 | | 1/2005 | Dunkley et al. |
| 2011/0277752 A1 | | 11/2011 | Cheu et al. |
| 2014/0088044 A1 | | 3/2014 | Rigas et al. |
| 2014/0088045 A1 | * | 3/2014 | Rigas ..................... A61K 9/007 128/202.21 |
| 2014/0130800 A1 | * | 5/2014 | Seeney ............. A61M 15/0065 128/203.15 |
| 2015/0136131 A1 | | 5/2015 | Holakovsky et al. |
| 2018/0093050 A1 | * | 4/2018 | Stenzler ............ A61M 15/0013 |
| 2018/0093051 A1 | * | 4/2018 | Stenzler ............ A61M 15/0021 |
| 2018/0140790 A1 | * | 5/2018 | Stenzler ............ A61M 15/0021 |
| 2018/0147371 A1 | * | 5/2018 | Stenzler ................ A61M 15/06 |
| 2021/0153545 A1 | * | 5/2021 | Zinovik ............... A61K 9/0075 |

FOREIGN PATENT DOCUMENTS

| | | | |
|---|---|---|---|
| CN | 103315402 | | 9/2013 |
| CN | 104126878 | | 11/2014 |
| EP | 0333334 | * | 2/1989 ............ A61M 15/00 |
| EP | 1208863 A2 | * | 5/2002 .......... A61M 11/001 |
| EP | 2399637 | | 12/2011 |
| EP | 3348156 | | 7/2018 |
| GB | 2461008 | | 12/2009 |
| JP | 2011505905 | | 3/2011 |
| RU | 2460677 | | 9/2012 |
| WO | 19910001656 | | 2/1991 |
| WO | 20070061987 | | 5/2007 |
| WO | 20090075794 | | 6/2009 |
| WO | 20150166344 | | 11/2015 |
| WO | 20150166350 | | 11/2015 |
| WO | 20150193498 | | 12/2015 |

OTHER PUBLICATIONS

Chinese Office Action for CN201680071159.X issued by the China National Intellectual Property Administration on Jan. 19, 2021, 14 pgs. including English translation.
International Search Report and Written Opinion from the European Patent Office, for PCT/IB2016/057455, issued on Feb. 21, 2017; 16 pgs.
Written Opinion of the International Preliminary Examining Authority, from the European Patent Office, for PCT/IB2016/057455, issued on Dec. 21, 2017; 9 pgs.
International Preliminary Report on Patentability from the European Patent Office, for PCT/IB2016/057455, issued on Apr. 9, 2018; 25 pgs.
Cohen et al., "GRAS Flavoring Substances," 27. GRAS Flavoring Substances. Food Technology for Flavoring Extract Manufacturers Association, 2015:69(8):40-59.
Russian Office Action issued for Russian patent application No. 2018126476, issued by the Patent office of the Russian Federation on Apr. 21, 2020; 10 pgs. Including English translation.
Chinese Office Action for CN Application No. 201680071159.X, issued by the China National Intellectual Property Administration dated Jun. 3, 2020; 15 pgs. Including English Translation.
Japanese Office Action for JP Application No. 2018-529303 issued by the Japanese Patent Office on Nov. 26, 2020; 6 pgs. including English Translation.

* cited by examiner

NICOTINE POWDER DELIVERY SYSTEM

This is a continuation application of U.S. patent application Ser. No. 16/064,173, filed 20 Jun. 2018, which is the § 371 U.S. National Stage of International Application No. PCT/IB2016/057455, filed 8 Dec. 2016, which claims the benefit of European Patent Application No. 15202712.4, filed 24 Dec. 2015, the disclosures of which are incorporated herein by reference.

This disclosure relates to nicotine powder delivery system that includes an inhaler article and a nicotine powder capsule disposed within the inhaler article. The nicotine powder capsule may rotate about a longitudinal axis when air flows through the inhaler article.

Dry powder inhalers (DPI) are known and are used to treat respiratory diseases by delivering a dry powder comprising a pharmaceutical, in aerosol form through inhalation to the patients' airways. For delivery into the lungs, particles in the range of 1 to 5 micrometers are preferred. In pharmaceutical dry powders, the active pharmaceutical ingredient (API) is agglomerated on the surface of larger carrier particles, such as lactose for example. DPI's operate complex mechanisms to ensure such agglomerates disperse, break up or disaggregate before the API can be inhaled into the lungs. Pharmaceutical dry powders containing lactose as a carrier can be in the range of 20 to 100 micrometers.

DPI's rely on the force of the patients' inhalation to entrain the powder from the device to subsequently break-up the powder into particles that are small enough to enter the lungs. Sufficiently high inhalation rates are required to ascertain correct dosing and complete disaggregation of the powder. Typically a large amount of API remains attached on the surface of the carrier and is deposited in the upper airways due to incomplete de-aggregation of the powder. Inhalation rates of existing DPI's are usually in the range of 20-100 liters/min (L/min). Existing DPI's are therefore only suitable for delivering dry powders to users in a manner that is different from the inhalation rate associated with smoking articles.

It would be desirable to provide a nicotine powder delivery system that provides nicotine particles to the lungs at inhalation or air flow rates that are within conventional smoking regime inhalation or air flow rates. It would also be desirable to provide deliver the nicotine powder system with an inhaler article that is a similar size and configuration as a conventional cigarette.

A nicotine powder delivery system includes an inhaler article and a nicotine powder capsule disposed within the inhaler article. Air flow management through the inhaler article may cause the pierceable nicotine powder capsule to rotate and release nicotine powder into the air flow.

The inhaler article includes an inhaler body extending between a mouthpiece portion and a distal end portion. A nicotine powder receptacle is disposed within the inhaler body and between the mouthpiece portion and the distal end portion. An air inlet port extends through the inhaler body and into the nicotine powder receptacle. A mouthpiece air channel fluidly connects the nicotine powder receptacle with a proximal end of the mouthpiece. A nicotine powder capsule containing nicotine powder is disposed within the nicotine powder receptacle. The nicotine powder capsule may rotate about a longitudinal axis when air flows from the air inlet port to the mouthpiece air channel.

A ready-to-consume nicotine capsule containing nicotine powder comprising particles comprising nicotine is described and may have only a single aperture through the nicotine capsule for releasing an aerosolized nicotine powder through the single aperture.

A method of inhaling nicotine includes the step of inhaling air through a nicotine powder inhaler where the nicotine powder inhaler includes a nicotine capsule having only a single aperture through the nicotine capsule. Nicotine powder is released through the single aperture and into the air, at an air flow rate of less than about 2 litres per minute, to deliver the nicotine powder to lungs of the user.

Advantageously, the nicotine powder delivery system described herein may provide a simple inhaler and capsule system that delivers nicotine at inhalation or air flow rates that are within conventional smoking regime inhalation or air flow rates. Advantageously, the nicotine powder delivery system may utilize a capsule having a single aperture for nicotine powder release. Advantageously, the single aperture may provide a controlled release of nicotine powder with each inhalation or "puff" of the nicotine powder delivery system. Advantageously, the single aperture may prevent a fast depletion of the nicotine powder. Advantageously, rotation of the nicotine powder capsule may suspend the nicotine powder and aerosolizes the nicotine powder in the inhalation air moving through the air flow channel of the inhaler article.

Flavour particles may be combined with the nicotine powder. These flavour particles may be larger than the nicotine particles and assist in transporting the nicotine particles into the lungs of the user while the flavour particles preferentially remain in the mouth or buccal cavity of the user.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof. The term "flavourant" or "flavour" preferably refers to compounds disclosed in the Flavor & Extract Manufacturers Association (FEMA) Flavor Ingredient Library and in particular in the GRAS Flavoring Substances publications 3 to 27, for example, see Hall, R. L. & Oser, B. L., Food Technology, February 1965 pg 151-197, and in the GRAS flavoring substances 27 S. M. Cohen et al., Food Technology August 2015 pg. 40-59, and intervening GRAS Flavoring Substances publications 4 to 26. For the purpose of this disclosure, nicotine is not considered as a flavourant or flavour.

The size of a particle, stated herein, preferably refers to the aerodynamic diameter of the particle. The aerodynamic diameter of a powder system is preferably measured with a cascade impactor.

This disclosure relates to nicotine powder delivery systems that include an inhaler article and a nicotine powder capsule containing nicotine powder is disposed within the inhaler article. The nicotine powder capsule may rotate about a longitudinal axis when air flows through the inhaler article. The nicotine powder capsule may be pierced to form only a single aperture (or no more than one aperture or less than two apertures) through the nicotine powder capsule. Nicotine powder and optional flavour particles may exit the single aperture during consumption. Air flow management though the inhaler article may cause the nicotine powder capsule to rotate or spin within the nicotine powder receptacle and release an aerosol of nicotine powder and optional flavour particles into the mouthpiece channel for delivery to the user.

The nicotine powder delivery system provides nicotine particles preferentially to the lungs of a user and optional flavour particles preferentially to the buccal or mouth cavity of a user. The relative particle sizes of the nicotine powder component and the optional flavour powder component may remain stable even when combined with each other and is preferably a free flowing powder. The nicotine powder may be delivered with a simple inhaler construction at inhalation or air flow rates that are within conventional smoking regime inhalation or air flow rates.

The inhaler article includes an inhaler body extending between a mouthpiece portion and a distal end portion and a nicotine powder receptacle disposed within the inhaler body and between the mouthpiece portion and the distal end portion. An air inlet port extends through the inhaler body and into the nicotine powder receptacle. A mouthpiece air channel is fluidly connected to the nicotine powder receptacle and a proximal end of the mouthpiece. Preferably the inhaler body may resemble a cigarette.

The air inlet port may be arranged and configured to cause the nicotine powder capsule to rotate or spin within the nicotine powder receptacle. The nicotine powder capsule may have an obround shape with circular cross-section extending a length along a central axis. The air inlet port may direct air into the nicotine powder receptacle in a direction that is substantially orthogonal to the longitudinal (central) axis of the nicotine powder capsule contained within the nicotine powder receptacle.

The air inlet port may be off-set from the longitudinal (central) axis of the nicotine powder capsule contained within the nicotine powder receptacle. The off-set air inlet may induce the nicotine powder capsule to rotate or spin within the nicotine powder receptacle during inhalation by the consumer. The air inlet port may be off-set from the longitudinal (central) axis of the nicotine powder capsule by about 2 mm, or about 3 mm, or about 4 mm. The one or more air inlet ports may have a diameter from about 0.5 to 1.5 mm, or about 0.7 to about 0.9 mm. Preferably, the air inlet port directs air tangent to the outer diameter of the nicotine powder capsule contained within the nicotine powder receptacle.

The nicotine powder receptacle preferably may has a circular cross-sectional shape extending (a length distance) along its central axis and forming a cylindrical nicotine powder receptacle. Preferably the nicotine powder receptacle defines a right circular cylinder with a radius and having a length extending along a central axis. The air inlet port may enter the nicotine powder receptacle tangentially to the cylindrical nicotine powder receptacle. There are two air inlet ports that enter the nicotine powder receptacle tangentially to the cylindrical nicotine powder receptacle. Preferably these air inlet ports oppose each other and the first air inlet port directs air tangentially to the cylindrical nicotine powder receptacle in a first direction and the second air inlet port directs air tangentially to the cylindrical nicotine powder receptacle in a second direction that opposes or is in the opposite direction as the first direction. These opposing air inlet ports may direct inhalation air at opposing sides of the nicotine powder capsule contained within the nicotine powder receptacle promoting the rotation of the nicotine powder capsule contained within the nicotine powder receptacle.

The nicotine powder receptacle preferably may have a circular cross-sectional shape with a first diameter. The nicotine powder capsule contained within the nicotine powder receptacle has a second diameter that is less than the first diameter. Preferably, the second diameter (of the nicotine powder capsule) may be in a range from about 80% to about 99%, or from about 90% to about 98% of the first diameter (of the nicotine powder receptacle). Preferably the diameter of the nicotine powder capsule may be about 0.5 to about 2 mm less than the diameter of the nicotine powder receptacle or from about 1 to about 2 mm less than the diameter of the nicotine powder receptacle. The nicotine powder receptacle may have a length in a range from about 10 mm to about 30 mm, or from about 15 mm to about 25 mm, or about 20 mm.

The end cap element may be formed of any pierceable material that has a resistance to draw (RTD) greater than about 120 mm WG or in a range from about 120 mm WG to about 200 mm WG or in a range from about 120 mm WG to about 150 mm WG. One useful material forming the end cap element may be cellulose acetate or high density cellulose acetate. As described below, a piercing element may pass through the end cap element and form a single aperture through the wall of the nicotine powder capsule. The material forming the end cap element may substantially close the hole formed in the material forming the end cap element once the piercing element is removed from the piercing element. The end cap element may have a length in a range from about 2 mm to about 20 mm, or from about 5 mm to about 15 mm, or from about 8 mm to about 12 mm, or about 10 mm.

The mouthpiece portion may be formed of any useful material. The mouthpiece portion has at least one airflow channel that fluidly connects the nicotine powder receptacle to the proximal end of the mouthpiece. The mouthpiece portion may have at least two parallel and coextensive airflow channels that fluidly connect the nicotine powder receptacle to the proximal end of the mouthpiece. The one or more mouthpiece airflow channels have a diameter of at least about 0.5 mm, and may be in a range from about 0.5 mm to about 2 mm, or from about 1 mm to about 2 mm. The one or more mouthpiece airflow channels may preferably be linear along the length of the mouthpiece portion. The mouthpiece portion may have a length in a range from about 10 mm to about 25 mm, or from about 10 mm to about 20 mm, or about 15 mm.

The nicotine powder delivery system may have an overall resistance to draw (RTD) that is less than 100 mm WG, or in a range from about 50 mm WG to about 100 mm WG. The nicotine powder delivery system may mimic the configuration of a cigarette. The nicotine powder delivery system or inhaler may have a length in a range from about 40 mm to about 110 mm, or from about 40 mm to about 80 mm and a diameter in a range from about 5 mm to about 10 mm, or in a range from about 7 mm to about 8 mm.

A nicotine powder capsule may be disposed within the nicotine powder receptacle. The nicotine powder capsule may be configured to rotate about its longitudinal or central axis when air flows from the one or more air inlet ports through the nicotine powder receptacle to the mouthpiece air channel. The capsule may be formed of an airtight material that may be pierced or punctured by the inhaler. The capsule may formed of a metallic or polymeric material that serves to keep contaminates out of the capsule but may be pierced or punctured by a piercing element prior to consumption of the powder within the capsule. The capsule may be formed of a polymer material. The polymer material may be hydroxypropylmethylcellulose (HPMC). Preferably, the capsule is a size 2 to size 4 capsule, or a size 3 capsule.

The nicotine powder capsule contains nicotine powder that comprises nicotine particles (also referred to as "nicotine powder" or "particles comprising nicotine") and optional flavour particles. The nicotine powder capsule may contain a predetermined amount of nicotine particles and optional flavour particles. The capsule may contain enough nicotine particles to provide at least 2 inhalations or "puffs"

of nicotine, or at least about 5 inhalations or "puffs" of nicotine, or at least about 10 inhalations or "puffs" of nicotine. Preferably, the capsule may contain enough nicotine particles to provide from about 5 to 50 inhalations or "puffs" of nicotine, or from about 10 to 30 inhalations or "puffs" of nicotine. Each inhalation or "puff" of nicotine particles may deliver from about 0.1 mg to about 3 mg of nicotine particles to the lungs of the user or from about 0.2 mg to about 2 mg of nicotine particles to the lungs of the user or about 1 mg of nicotine particles to the lungs of the user. Preferably, about 50 to about 150 micrograms of nicotine is delivered to the lungs of the user with each "puff".

The capsule may hold or contain at least about 5 mg of nicotine particles or at least about 10 mg of nicotine particles. Preferably, the capsule may hold or contains less than about 30 mg of nicotine particles or less than about 25 mg of nicotine particles, or less than 20 mg of nicotine particles. The capsule may hold or contain from about 5 mg to about 30 mg of nicotine particles or from about 10 mg to about 20 mg of nicotine particles.

When flavour particles are blended or combined with the nicotine particles within the capsule, the flavour particles are present in an amount that provides the desired flavour to each inhalation or "puff" delivered to the user.

The particles comprising nicotine may have any useful size distribution for inhalation delivery preferentially into the lungs of a user. The powder system may have at least about 40% or at least about 60%, or at least about 80%, by weight of the nicotine of the powder system comprised in particles having a particle size of about 10 micrometres or less. The powder system may have at least about 40% or at least about 60%, or at least about 80%, by weight of the nicotine of the powder system comprised in particles having a particle size of about 5 micrometres or less. The powder system may have at least about 40% or at least about 60%, or at least about 80%, by weight of the nicotine of the powder system comprised in particles having a particle size in a range from about 1 micrometer to about 3 micrometres.

Nicotine in the nicotine powder or nicotine particles may be a pharmaceutically acceptable free-base nicotine, or nicotine salt or nicotine salt hydrate. Useful nicotine salts or nicotine salt hydrates include; nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect. For example: nicotine salicylate may be administered for fever relief, as an anti-inflammatory or painkiller; nicotine fumarate may be administered to treat multiple sclerosis; and nicotine mono-pyruvate may be administered for treating chronic obstructive pulmonary disease (COPD) or for weight loss.

The particles comprising nicotine may include an amino acid. Preferably the amino acid may be leucine such as, L-leucine. Providing an amino acid such as L-leucine with the particles comprising nicotine, especially coating the nicotine or particles comprising nicotine with the amino acid, may reduce adhesion forces of the particles comprising nicotine and may reduce attraction between nicotine particles and thus reduce agglomeration of nicotine particles. Similarly, adhesion forces to particles comprising flavour may also reduced thus agglomeration of nicotine particles with flavour particles may also reduced. The powder system described herein thus may be a free flowing material and possess a stable relative particle size of each powder component even when the nicotine particles and the flavour particles are combined.

Preferably, the nicotine may be a surface modified nicotine salt where the nicotine salt particle is a coated particle. A preferred coating material is L-leucine. One particularly useful nicotine powder is an L-leucine coated nicotine bitartrate.

The nicotine powder capsule may optionally include flavour particles. The flavour particles may have any useful size distribution for inhalation delivery selectively into the mouth or buccal cavity of a user.

The powder system may have at least about 40% or at least about 60%, or at least about 80%, by weight of the flavour of the powder system comprised in particles having a particle size of about 20 micrometres or greater. The powder system may have at least about 40% or at least about 60%, or at least about 80%, by weight of the flavour of the powder system comprised in particles having a particle size of about 50 micrometres or greater. The powder system may have at least about 40% or at least about 60%, or at least about 80%, by weight of the flavour of the powder system comprised in particles having a particle size in a range from about 50 micrometer to about 150 micrometres.

Flavourants or flavours may be provided as a solid flavour (at room temperature of about 22 degrees centigrade and one atmosphere pressure) and may include flavour formulations, flavour-containing materials and flavour precursors. The flavourant may include one or more natural flavourants, one or more synthetic flavourants, or a combination of natural and synthetic flavourants. Flavourants as described herein are organoleptic compounds, compositions, or materials that are selected and utilized to alter or are intended to alter the taste or aroma characteristics of the nicotine powder component during consumption or inhalation thereof.

Flavourants or flavours refer to a variety of flavour materials of natural or synthetic origin. They include single compounds and mixtures. Preferably the flavour or flavourant has flavour properties that enhance the experience of the nicotine powder component during consumption. Preferably, the flavour is chosen to provide an experience similar to that resulting from smoking a combustible smoking article. For example, the flavour or flavourant may enhance flavour properties such as mouth fullness and complexity. Complexity is generally known as the overall balance of the flavour being richer without dominating single sensory attributes. Mouth fullness is described as perception of richness and volume in the mouth and throat of the consumer.

Suitable flavours include, but are not limited to, any natural or synthetic flavour, such as tobacco, smoke, menthol, mint (such as peppermint and spearmint), chocolate, licorice, citrus and other fruit flavours, gamma octalactone, vanillin, ethyl vanillin, breath freshener flavours, spice flavours such as cinnamon, methyl salicylate, linalool, bergamot oil, geranium oil, lemon oil, and ginger oil, and the like.

Other suitable flavours may include flavour compounds selected from the group consisting of an acid, an alcohol, an ester, an aldehyde, a ketone, a pyrazine, combinations or blends thereof and the like. Suitable flavour compounds may be selected, for example, from the group consisting of phenylacetic acid, solanone, megastigmatrienone, 2-heptanone, benzylalcohol, cis-3-hexenyl acetate, valeric acid, valeric aldehyde, ester, terpene, sesquiterpene, nootkatone, maltol, damascenone, pyrazine, lactone, anethole, iso-s valeric acid, combinations thereof, and the like.

Further specific examples of flavours may be found in the current literature, and are well-known to the person skilled in the art of flavouring, i.e. of imparting an odor or taste to a product.

The flavourant may be a high potency flavourant, and may be used and detected at levels that would result in less than 200 parts per million in inhalation air flow. Examples of such flavourants are key tobacco aroma compounds such as beta-damascenone, 2-ethyl-3,5-dimethylpyrazine, phenylacetaldehyde, guaiacol, and furaneol. Other flavourants may only be sensed by humans at higher concentration levels. These flavourants, which are referred to herein as the lower potency flavourants, are typically used at levels that results in orders of magnitude higher amounts of flavourant released into the inhalation air. Suitable lower potency flavourants include, but are not limited to, natural or synthetic menthol, peppermint, spearmint, coffee, tea, spices (such as cinnamon, clove and ginger), cocoa, vanilla, fruit flavours, chocolate, eucalyptus, geranium, eugenol and linalool.

The particles comprising flavour may include a compound to reduce adhesion forces or surface energy and resulting agglomeration. The flavour particle may be surface modified with an adhesion reducing compound to form a coated flavour particle. One preferred adhesion reducing compound is magnesium stearate. Providing an adhesion reducing compound such as magnesium stearate with the flavour particle, especially coating the flavour particle, reduces adhesion forces of the particles comprising flavour and may reduce attraction between flavour particles and thus reduce agglomeration of flavour particles. Thus agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably is free flowing.

Conventional formulations for dry powder inhalation typically contain carrier particles that serve to increase the fluidization of the active particles since the active particles may be too small to be influenced by simple airflow though the inhaler. These carrier particles are usually a saccharide such as lactose or mannitol that have a particle size greater than about 50 micrometres. The carrier particles are utilized to improve the dose uniformity by acting as a diluent or bulking agent in a formulation. Carrier particles such as lactose or mannitol are not considered flavourants or flavour material in this disclosure.

The powder system utilized with the nicotine powder delivery system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates. In addition, since the nicotine is carrier-free or substantially free of a saccharide such as lactose or mannitol, the airflow path of the inhaler may have simple geometry or a simple configuration.

The nicotine powder and a flavour may be combined in a single capsule. As described above, the nicotine powder and a flavour may each have reduced adhesion forces that result in a stable powder formulation where the particle size of each component does not substantially change when combined. Alternatively, the powder system may include nicotine particles contained within a single capsule and the flavour particles contained within a second capsule.

The nicotine particles and a flavour particles may be combined in any useful relative amount so that the flavour particles are detected by the user when consumed with the nicotine particles. Preferably the nicotine particles and flavour particles may form at least about 90% wt or at least about 95% wt or at least about 99% wt or 100% wt of the total weight of the powder system.

This nicotine powder delivery system and inhaler may be less complex and may have a simplified powder storage and airflow path as compared to existing DPIs. The nicotine powder delivery system and inhaler described herein may not need a typical carrier ingredient, such as lactose, as described above. Advantageously, rotation of the nicotine powder capsule within the inhaler aerosolizes the nicotine powder and may assist in maintaining a free flowing powder. Thus, the inhaler does not require the typical high inhalation rates of conventional DPIs to deliver the dry nicotine powders described above deep into the lungs.

The nicotine inhaler according to this invention operates may use a flow rate of less than about 5 L/min or less than about 3 L/min or less than about 2 L/min or about 1.6 L/min. Preferably, the flow rate is in a range from about 1 L/min to about 3 L/min or from about 1.5 L/min to about 2.5 L/min. Preferably, the inhalation rate or flow rate is similar to that of Health Canada smoking regime, that is about 1.6 L/min.

The nicotine inhaler described herein may be used by a consumer like smoking a conventional cigarette or vaping an electronic cigarette. Such smoking or vaping is characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

A piercing element, such as a metal or rigid needle, forms a single aperture through the capsule. The capsule is received within the nicotine powder receptacle and the piercing element may pierce the aperture into the capsule that is received in the nicotine powder receptacle. The piercing element may pass through the end cap element.

The piercing element may be included on or within an article or packaging container housing a plurality of nicotine powder delivery systems. The piercing element may be fixed to the article or packaging container. Preferably, a single piercing element may be fixed to the article or packaging container and the user may manually puncture the nicotine capsule contained within the nicotine powder inhaler by inserting the piercing element through the nicotine powder inhaler end cap and into the nicotine capsule contained within the nicotine powder receptacle to form the single aperture through the capsule. The user then withdraws the nicotine powder inhaler from the piercing element and consumes the nicotine powder.

Alternatively, there may be an equal number of piercing elements and nicotine powder delivery systems within an article or packaging container. A piercing element is registered and inserted into each respective nicotine powder inhaler end cap and into the nicotine capsule contained within the nicotine powder receptacle to form the single aperture though each capsule. The user then withdraws each nicotine powder inhaler from its respective piercing element and consumes the nicotine powder.

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Figure 2:
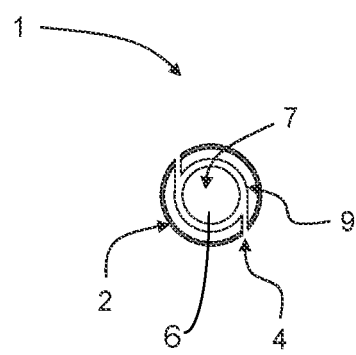
Figure 3:
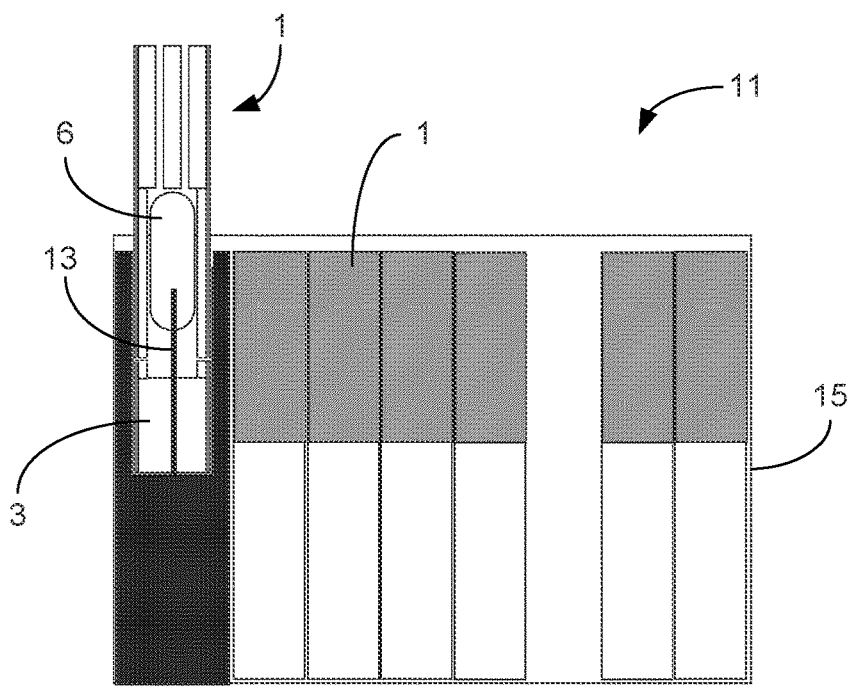
Figure 4:
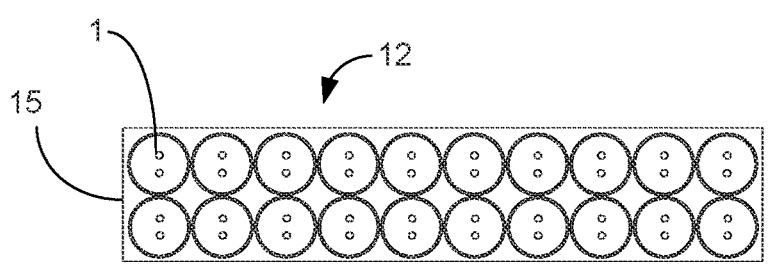

FIGS. 1-2 are schematic diagrams of illustrative nicotine powder delivery systems 1. FIGS. 3-4 are schematic diagrams of illustrative articles 11, 12 packaging illustrative nicotine powder delivery systems 1. The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Referring now to FIG. 1 and FIG. 2, the nicotine powder delivery system includes an inhaler article 1 that include an inhaler body 2 extending between a mouthpiece portion 5 and a distal end portion 3 or end cap element 3. A nicotine powder receptacle 9 defining a capsule cavity 8 is disposed within the inhaler body 2 and between the mouthpiece portion 5 and the distal end portion 3. An air inlet port 4 extends through the inhaler body 2 and into the nicotine powder receptacle 9. A mouthpiece air channel 10 fluidly connects the nicotine powder receptacle 9 with a proximal end of the mouthpiece 5. A nicotine powder capsule 6 is disposed within the nicotine powder receptacle 9. Particles comprising nicotine 7 and optional particles comprising flavour is disposed within the nicotine powder capsule 6. As described above, a piecing element may pass thorough the distal end portion 3 or end cap element 3 and form a single aperture into the nicotine powder capsule 6 for consumption. Air flow management through the air inlet ports 4 causes the nicotine powder capsule 6 to rotate about its longitudinal axis when air flows from the air inlet port 4 downstream to the mouthpiece air channel 10.

FIG. 3 is a side view schematic diagram of an illustrative article 11 packaging illustrative nicotine powder delivery systems 1. The article 11 includes a container 15 that contains a plurality of nicotine powder delivery systems 1 and a single piercing element 13. A user removes the nicotine powder delivery system 1 from the container 15 and inserts the end cap element 3 of the nicotine powder delivery system 1 onto the piercing element 13 until the piercing element 13 pierces through the capsule 6 forming a single aperture through the capsule 6. Then the user removes the pierced nicotine powder delivery system 1 from the piercing element 13 and consumes the nicotine powder. The piercing element 13 is fixed to the article 11. The nicotine powder delivery system 1 being pierced is shown in cross-section to illustrate the location of the piercing element 13.

Figure 5:
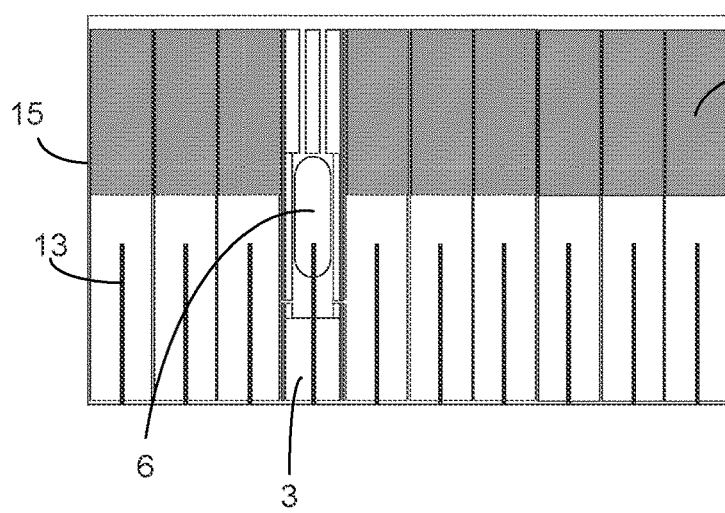

FIG. 4 is a top view schematic diagram of an illustrative article 12 packaging illustrative nicotine powder delivery systems 1. FIG. 5 is a side view schematic diagram of an illustrative article 12 packaging illustrative nicotine powder delivery systems 1. The article 12 includes a container 15 that contains a plurality of nicotine powder delivery systems 1 and an equal number of piercing elements 13 and nicotine powder delivery systems 1 within the packaging container 12.

Here the piercing element 13 is preloaded onto each nicotine powder delivery system 1 so that each piercing element passes through the capsule 6 forming a single aperture through the capsule 6. The user removes the pierced nicotine powder delivery system 1 from the piercing element 13 and consumes the nicotine powder. The plurality of piercing elements 13 are fixed to the article 12. One nicotine powder delivery system 1 is shown in cross-section to illustrate the location of the respective piercing element 13. The piercing element 13 is registered and inserted into each respective nicotine powder inhaler end cap 3 and into the nicotine capsule 6 contained within the nicotine powder receptacle. The user then withdraws each nicotine powder inhaler 1 from its respective piercing element 13 and consumes the nicotine powder.

The invention claimed is:
1. A nicotine powder delivery system, comprising:
an inhaler article comprising;
an inhaler body extending between a mouthpiece portion and a distal end portion;
a nicotine powder receptacle disposed within the inhaler body and between the mouthpiece portion and the distal end portion;
an air inlet port extending through the inhaler body and into the nicotine powder receptacle;
a mouthpiece air channel fluidly connecting the nicotine powder receptacle with a proximal end of the mouthpiece portion, wherein the mouthpiece air channel comprises at least two parallel and coextensive airflow channels that fluidly connect the nicotine powder receptacle to the proximal end of the mouthpiece portion, and extend from the nicotine powder receptacle to the proximal end of the mouthpiece portion;
a nicotine powder capsule containing nicotine powder is disposed within the nicotine powder receptacle, wherein the nicotine powder capsule rotates about a longitudinal axis when air flows from the air inlet port to the mouthpiece air channel.

2. The nicotine powder delivery system according to claim 1, wherein the air inlet port is off-set from the longitudinal axis.

3. The nicotine powder delivery system according to claim 1, wherein the nicotine powder receptacle has a circular cross-sectional shape and the air inlet port enters the nicotine powder receptacle tangential to the nicotine powder receptacle.

4. The nicotine powder delivery system according to claim 3, wherein the air inlet port comprises a first air inlet port and a second air inlet port.

5. The nicotine powder delivery system according to claim 4, wherein the first air inlet port is tangential to the nicotine powder receptacle and the second air inlet port is tangential to the nicotine powder receptacle.

6. The nicotine powder delivery system according to claim 5, the first air inlet port opposes the second air inlet port.

7. The nicotine powder delivery system according to claim 1, wherein the nicotine powder receptacle has a circular cross-sectional shape and a first diameter and the nicotine powder capsule has a second diameter that is less than the first diameter, and the second diameter is in a range from about 80% to about 99% of the first diameter.

8. The nicotine powder delivery system according to claim 1, wherein distal end portion has an end-cap element that has a resistance to draw (RTD) greater than about 120 mm WG and the nicotine powder delivery system has a resistance to draw (RTD) in a range from about 50 mm WG to about 100 mm WG.

9. The nicotine powder delivery system according to claim 1, wherein the nicotine powder comprises particles comprising nicotine and having a mass median aerodynamic diameter in a range from about 1 micrometres to about 3 micrometres.

10. The nicotine powder delivery system according to claim 9, wherein the particles comprising nicotine comprises nicotine salt or nicotine salt hydrate.

11. The nicotine powder delivery system according to claim 9, wherein the particles comprising nicotine comprise an amino acid coating.

12. The nicotine powder delivery system according to claim 9, wherein the nicotine powder capsule contains particles comprising flavour and having a mass median aerodynamic diameter in a range from about 50 micrometres to about 150 micrometres.

13. The nicotine powder delivery system according to claim 1, further comprising a piercing element that passes through the distal end portion and pierces a single aperture into the nicotine powder capsule, wherein the piercing element is a single rigid needle and the piercing element is fixed to an article that is separate from the inhaler article.

14. An article containing a plurality of the nicotine powder delivery systems according to claim 13, wherein the piercing element is fixed to the article and the piercing element passes into the nicotine powder receptacle and pierces a single hole into the nicotine powder capsule and the nicotine powder delivery system is removed from the piercing element and article for consumption.

15. The nicotine powder delivery system according to claim 13, wherein the nicotine powder capsule has only a single aperture through the nicotine powder capsule for releasing aerosolized nicotine powder through the single aperture.

16. A method of inhaling nicotine, comprising:
inhaling air through a nicotine powder delivery system according to claim 1 the nicotine powder capsule having only a single aperture through the nicotine powder capsule and releasing the nicotine powder through the single aperture and into the air, at an air flow rate of less than about 2 litres per minute to deliver the nicotine powder to lungs of a user.

17. The method according to claim 16, wherein the inhaling air step rotates the nicotine capsule about the longitudinal axis when releasing the nicotine powder through the single aperture and into the air.

18. An article containing a plurality of the nicotine powder delivery systems according to claim 1, wherein a plurality of piercing elements are fixed to the article, wherein the number of piercing elements is equal to the number of nicotine powder delivery systems.

19. The article according to claim 18, wherein each of the plurality of piercing elements is registered and inserted into a corresponding nicotine powder capsule and forming a single aperture in the nicotine powder capsule.

20. The nicotine powder delivery system according to claim 1, wherein the nicotine powder receptacle has a circular cross-sectional shape and a first diameter and the nicotine powder capsule has a second diameter that is less than the first diameter, and the second diameter is in a range from about 90% to about 98% of the first diameter.

* * * * *